United States Patent [19]

Häfele et al.

[11] Patent Number: 5,570,129
[45] Date of Patent: Oct. 29, 1996

[54] METHOD AND APPARATUS FOR CORRECTING THE WHITE BALANCE OF A VIDEO COLOR PICTURE SIGNAL

[75] Inventors: Ulrich Häfele, Knittlingen; Michael Vögele, Kämpfelbach; Jean-Pierre Heinrichs, Bretten, all of Germany

[73] Assignee: Richard Wolf GmbH, Knittlingen, Germany

[21] Appl. No.: 521,155

[22] Filed: Aug. 30, 1995

[30] Foreign Application Priority Data

Sep. 3, 1994 [DE] Germany .......................... 44 31 491.4

[51] Int. Cl.⁶ ................................ H04N 9/73; H04N 9/64
[52] U.S. Cl. .......................... 348/223; 348/225; 348/655
[58] Field of Search ...................................... 348/223, 225, 348/228, 655, 659, 45, 68, 71; H04N 9/73, 9/64

[56] References Cited

U.S. PATENT DOCUMENTS 4,831,437  5/1989  Nishioka et al. .......................... 358/98
5,111,281  5/1992  Sekiguchi .................................. 358/29
5,177,599  1/1993  Takagi et al. ............................ 348/228
5,223,921  6/1993  Haruki et al. ............................ 348/223

FOREIGN PATENT DOCUMENTS 1-28693  6/1986  Japan .............................. H04N 9/730
2-31586  9/1989  Japan .............................. H04N 9/730

Primary Examiner—John K. Peng
Assistant Examiner—Glenton B. Burgess
Attorney, Agent, or Firm—Panitch, Schwarze, Jacobs & Nadel, P.C.

[57] ABSTRACT

The color quality of a received color picture signal is detected by a device for measuring the intensity of at least the red component and the green component of the picture signal. A microprocessor determines a correction value for the white balance correction on the basis of the detected color quality and corresponding to selectable correction values, stored in a memory, for each color component. The method and apparatus permit an application specific correction of the white balance, particularly for use in endoscopic systems, such as video endoscopes and endoscope cameras, to be used in different body organs which cause different color shifts.

20 Claims, 3 Drawing Sheets

METHOD AND APPARATUS FOR CORRECTING THE WHITE BALANCE OF A VIDEO COLOR PICTURE SIGNAL

FIELD OF THE INVENTION

The invention pertains to a method and a device for the correction of the white balance of a video color picture signal in which the color quality of a received signal is first detected.

BACKGROUND OF THE INVENTION

In the past, the primary field of usage of endoscopy was in diagnostics. In diagnosnics the doctor observes with the naked eye the hollow organ to be examined. The eye possesses high brightness and color dynamics, which results in the fact that the attainable imaging quality, with respect to resolution and color representation, is almost entirely dependent on the endoscope that is being used.

In surgery, however, other requirements are placed on an endoscopic system different from those in diagnostics. In the case of a surgical operation, the picture of the operating field must be available to the entire operating team, since several people carry out the surgical operation in cooperation.

As a result, observing the operating field with the naked eye through an endoscope is not adequate. For that reason, a video camera is mounted on the proximal end of the endoscope, or else a video endoscope with a distally mounted CCD sensor is used, so that the operating field can be shown on a monitor. With the use of CCD cameras, however, several problems arise as well, since a CCD sensor does not possess the dynamics, the sensitivity, and the spectral characteristics of the eye. This is especially important with regard to the representation of color. According to one possibility it is worthwhile to try to optimize the representation of color from the point of view of the color variations that occur in an endoscopic system. The optimization should be carried out as automatically as possible, so that the operating team can concentrate on the operation, and not have to concern itself with the technology.

In the case of an endoscopic examination of a hollow organ of the body, the endoscope is introduced into the body cavity or the hollow organ to be examined. Illumination light makes its way through light guide fibers in the endoscope and into the body cavity, where it illuminates the hollow organ. In order to obtain a true reproduction of the color, the illumination light should not be spectrally influenced by the hollow organ. However, depending on the nature of the hollow organ, that is not the case. A portion of the illumination light penetrates, for example, into the mucous membrane inside the hollow organ, and this membrane acts as an absorption filter. As a result, the mucous membrane acts in turn as a narrow-band spectral illumination source, since the penetrating illumination light is re-radiated in a filtered fashion from the surface of the mucous membrane, and in turn illuminates with red light the object to be observed.

This light absorption behavior differs, depending upon the hollow organ being examined. Thus, the light absorption behavior plays no role in the joint area, whereas in the stomach, where mucous membranes that are heavily supplied with blood can be found, it leads to a color shift in the red direction. For any given organ, the strength of the red shift depends upon the observation distance and the observation and illumination angle of the endoscope. The shorter the observation distance or the closer the endoscope is to the mucous membrane, the more strongly the mucous membrane is trans-illuminated, which leads to a stronger red shift.

If the angle of observation or illumination becomes greater, then the intensity of the illumination light becomes greater in the edge areas. In this case, the mucous membrane is strongly trans-illuminated there. This effect occurs in a particularly severe way in gastroscopy and coloscopy, for which the viewing and illumination angle amounts to at least 120°. In such cases, tube-like hollow organs (i.e., esophagus, intestines) are being examined in which the mucous membrane is located very close to the instrument. In combination with the large viewing and illumination angle, this leads to a very large red shift in these places. However, this application-specific color shift is not taken into account by industrial video cameras.

U.S. Pat. No. 5,111,281 describes a color correction device for a video endoscope, having means for detecting the color quality of a color picture signal and means for the pixel-by-pixel execution of a dynamic color correction. Since the correction is carried out pixel-by-pixel, the known device is not able to distinguish between strong colors, red in particular, that occur in a point-like fashion, and increases in color that affect the entire picture. As a result, the known device also corrects increases in color that occur in a point-like fashion, and thus has poor color differentiation.

In U.S. Pat. No. 4,831,437 a video endoscope is described which is provided with a device for color balance. By means of this device, however, only the static color variations, such as those caused by light guide cable, endoscope, and illumination source, can be regulated in the endoscopic system. This means that dynamic color variations, such as those which can be caused by the mucous membrane during an operation, are not compensated for.

In addition, U.S. Pat. No. 4,831,437 shows a specialized device for carrying-out an automatic white balance which eliminates the color error caused by the ambient light. Spectral differences of the components being used in the endoscopic system, such as light guide, light source and endoscope, are also compensated for. For the white balance, the device has a balloon-shaped balance accessory with a white coating on the inside, through the opening of which the endoscope is inserted. It is thereby ensured that the ambient light that disturbs the balance does not mix with the illumination light. As a result, a white field of observation located in front of the endoscope is also shown in white on the monitor. If, however, a hollow organ is examined with the endoscope after the white balance has been carried out, a shift in the red direction, results from the mucous membrane.

SUMMARY OF THE INVENTION

It is therefore an object of the invention to provide a method and an apparatus for correction of the white balance of a video color picture signal which can ensure a maximum color differentiation of the color picture and can compensate for a specific red shift in the color picture signal.

A method for correcting the white balance of a video color picture signal which accomplishes the above-mentioned object comprises the following steps:

a) detecting a color quality of the color picture signal;

b) determining correction values for correction of the color picture signal present after the white balance, for each individual color component in dependency upon pre-set operating conditions;

c) correcting the color picture signal corresponding to the white balance by means of the correction values determined in step b), in dependency upon a relationship of the red component detected in step a) to the brightness portion of the detected color quality of the color picture signal.

Preferably, several sets of correction values that correspond to the operating conditions are stored ahead of time in a storage step, whereby in step b) the correction values that correspond to these sets are read from a storage medium.

For optimization of the color differentiation, the method in accordance with the invention additionally includes an integration step d) for integration of at least a portion of the color components of the video color picture signal over one field period thereof. Preferably, the integration step d) integrates only red color components R and green color components G, and the correction step c) corrects the color picture signal following the white balance, in dependency upon the relationship R/(R+G).

It is expedient if the sets of correction values stored in the above-mentioned storage step, or several correction value functions stored ahead of time, are read in dependency on the relationship R/(R+G).

In conjunction with this, the stored sets of correction values or correction value functions can be linearly or non-linearly dependent upon the relationship of the red component to the brightness portion of the color picture signal.

The method in accordance with the invention can also be used, in particular, for the correction of the white balance of video color picture signals with video endoscopes or endoscope cameras.

The apparatus in accordance with invention for the correcting the white balance of a video color picture signal includes a detection device for detecting the color quality of a received color picture signal, and is characterized by:

Means for determining correction values for correction of the white balance for each individual color component in dependency upon pre-set operating conditions, and Correction members for correcting the color components of the color picture signal corresponding to the white balance, by means of the determined correction values in dependency upon a relationship of the red component to the brightness portion corresponding to the color quality detected by the detection device.

The detection device has members for measuring the intensity of the red component R and the green component G of the color picture signal, and integration and retention members for integration and retention of the intensity value of both the red component R and the green component G over one field period of the received color picture signal.

The correction device includes an arithmetic unit for calculating an approximated brightness signal, both from the red component R that was integrated and retained over one field period by the integration and retention members and from the green component G that was integrated and stored over one field period, for calculation of a quotient R/(R+G) from an instantaneously measured intensity of the red component and the brightness signal and for determination of the correction value. The arithmetic unit may comprise, for example, a microprocessor. The latter can have a write-read memory as the storage means.

This write-read memory stores several pre-set sets of correction values dependent upon the quotient R/(R+G) and upon the pre-set operating conditions in the form of look-up tables, whereby the microprocessor reads, from the look-up table that corresponds with the current operating conditions, the appropriate correction value on the basis of the quotient R/(R+G) calculated from the instantaneously measured red component R and brightness signal R+G.

Functionally connected with the input of the microprocessor is a control unit for selection of one of several sets of correction values stored in the write-read memory or of one of several correction value functions dependent on the quotient of the instantaneous red component R and the approximately calculated brightness signal R+G. For generation of a DC voltage corresponding to the respective color components, the microprocessor is connected on the output side to correction voltage generators, one of which is allocated to each of the color components and receives from the microprocessor the respective selected correction value for the particular color component. Each correction voltage generator has a digital-analog converter or a digital potentiometer, which generates an analog DC correction voltage.

In addition, the output of each digital analog converter generating the respective correction voltage is connected with the input of a voltage-controlled amplifier, from which a different input is connected with a particular output of a white balance device, which is in turn functionally coupled with the control unit for carrying-out an automatic white balance. The outputs of the three voltage-controlled amplifiers each lead to inputs of a matrix circuit for generation of component signals.

BRIEF DESCRIPTION OF THE DRAWINGS

The foregoing summary, as well as the following detailed description of preferred embodiments of the invention, will be better understood when read in conjunction with the appended drawings which show further features and advantages of the invention. For the purpose of illustrating the invention, there are shown in the drawings embodiments which are presently preferred. It should be understood, however, that the invention is not limited to the precise arrangements and instrumentalities shown. It can also include combinations of individual features shown, described and/or claimed. In the drawings:

DETAILED DESCRIPTION OF PREFERRED EMBODIMENTS

Figure 1:
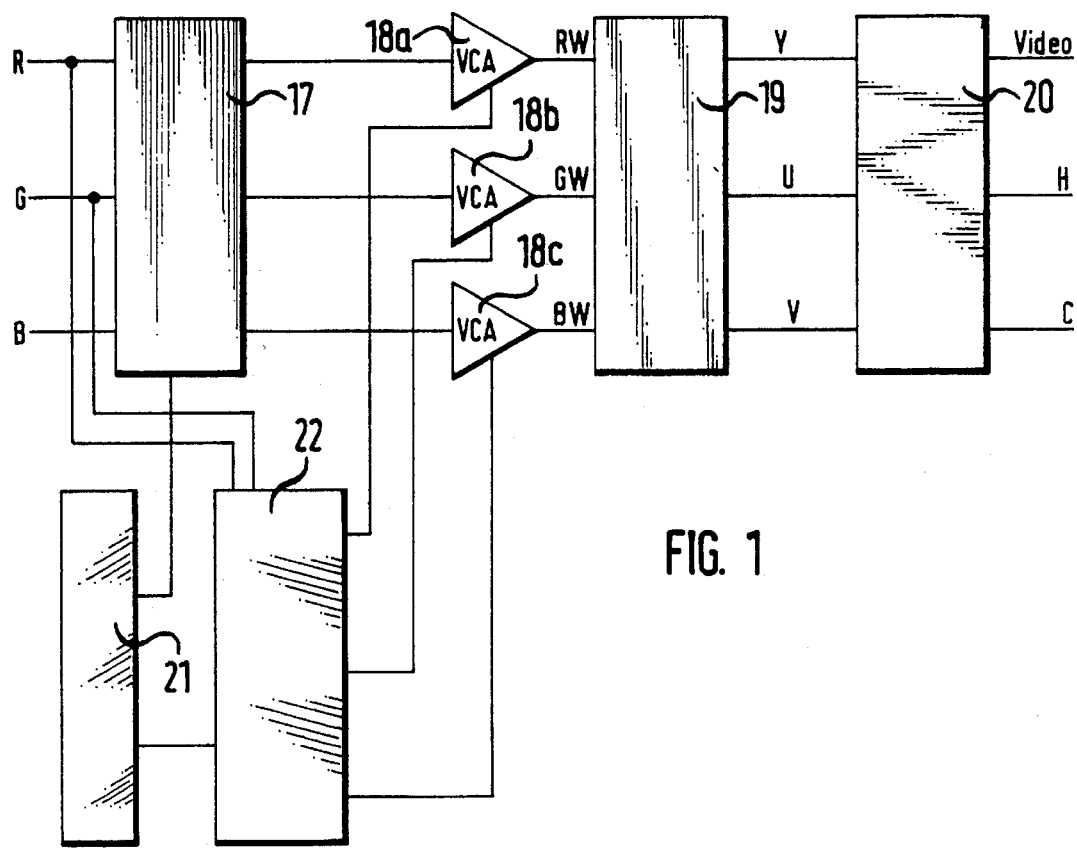
FIG. 1 is a block circuit diagram of a correction device in accordance with the invention.

In FIG. 1 video camera output signals R, G, and B are present at the input of a device 17 for automatic white balance. The device 17 is known per se, and is described in EP-0530738A, for example. It is controlled by a control unit 21. When a white balance button is actuated, an automatic white balance is carried out, as will be described in more detail later.

The balanced signals, that is the color components R, G, and B, proceed from the output of the device 17 respectively to an input of voltage-controlled amplifiers 18a, 18b and 18c, which are designated "VCA" in the following. The control inputs are each connected with a correction voltage generator 22b, 22c, 22d. With the aid of the VCAs 18a, 18b and 18c and the correction voltage generators 22b, 22c and 22d, the white balance can be corrected in an application-specific manner, in order to compensate for the color shift that occurs in the hollow organ of the body as a result of the mucous membrane. The VCAs 18a, 18b and 18c are triggered by the correction voltage generators 22b, 22c and 22d, respectively, with a correction voltage $U_{RW}$, $U_{GW}$, $U_{BW}$. The level of amplification of the VCAs is adjusted with the aid of these voltages. The thus-corrected signals RW, GW, BW are present at the input of a matrix 19, and are there converted into the component signals Y, U, V there. A modulator 20 connected behind the matrix 19 converts the component signals Y, U and V into the brightness signal H, the chromatic signal C and the video signal (video). The matrix 19 and the modulator 20 are common integrated complex components.

Figure 2:
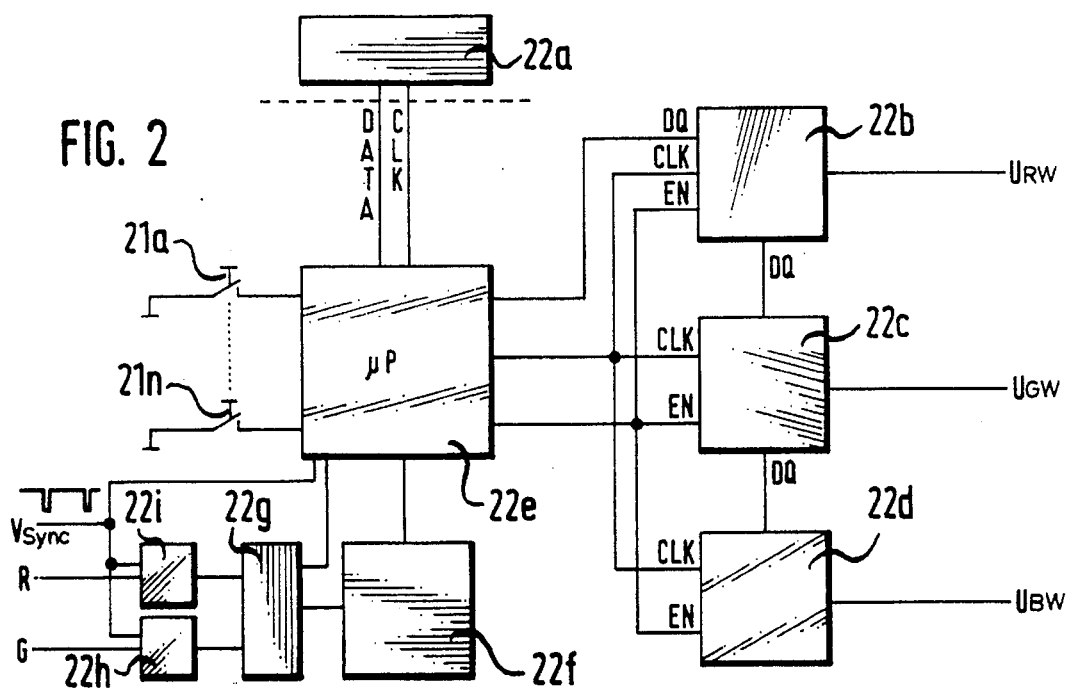
FIG. 2 is a block circuit diagram of the detection and correction device shown in FIG. 1.

As shown in FIGS. 1 and 2, the detection device 22 receives at its input the red color component R and the green color component G of the color picture signal, along with a synchronization pulse $V_{sync}$. In accordance with the invention, the correction device, as it is shown in FIGS. 1 and 2, carries out a dynamic white balance correction. The detection device measures the red portion and the green portion of the color picture and forms therefrom a signal that corresponds to the color quality, such that the measured red portion is set relative to a measured brightness portion of the picture. If the quotient of the red portion and the brightness portion exceeds a certain value, then it can be assumed that an increased red portion is present which is unusually large in a picture, that is a color shift in the red direction caused by the mucous membrane of the hollow organ of the body.

In the embodiment, only the red portion and green portion of the color components are measured. The green portion of the picture contributes most to the brightness signal H of the color picture, the blue portion least. The brightness signal H is composed of the color components R, G and B in the following way:

$$H=0.30R+0.59G+0.11B.$$

This equation results from the eye sensitivity curve for a light-adapted eye. Since the blue portion thus contributes least to the brightness signal, only the red portion R and the green portion G are measured, and the blue portion B is ignored.

The device 22 includes an arithmetic unit with a microprocessor 22e. The latter is functionally connected to the control unit 21, which is shown schematically in FIG. 2 by means of the buttons or keys 21a, . . . 21n. On these keys, n different operation- or application-specific settings can be selected, and, in addition, the color setting can be manually adjusted. Depending upon the setting selected, the microprocessor 22e calculates or reads from a table, which is stored in a write-read memory 22a, the correction values which correspond to the current application or operating condition for each color component, and which are output to the correction voltage generators 22b, 22c and 22d, which act as the digital-analog converters.

This write-read memory 22a can be located in an endoscope, for example, and contains, in addition to balance data for the video endoscope, an identifier by means of which the field of use of the endoscope, and thus also the optimum white balance function therefor, can be specified and automatically switched to a correction value function stored in the write-read memory 22a of the microprocessor 22e. In the write-read memory 22a, can be stored, in addition, data which do not relate to the optimized correction values for the instrument being used at present.

Figure 3:
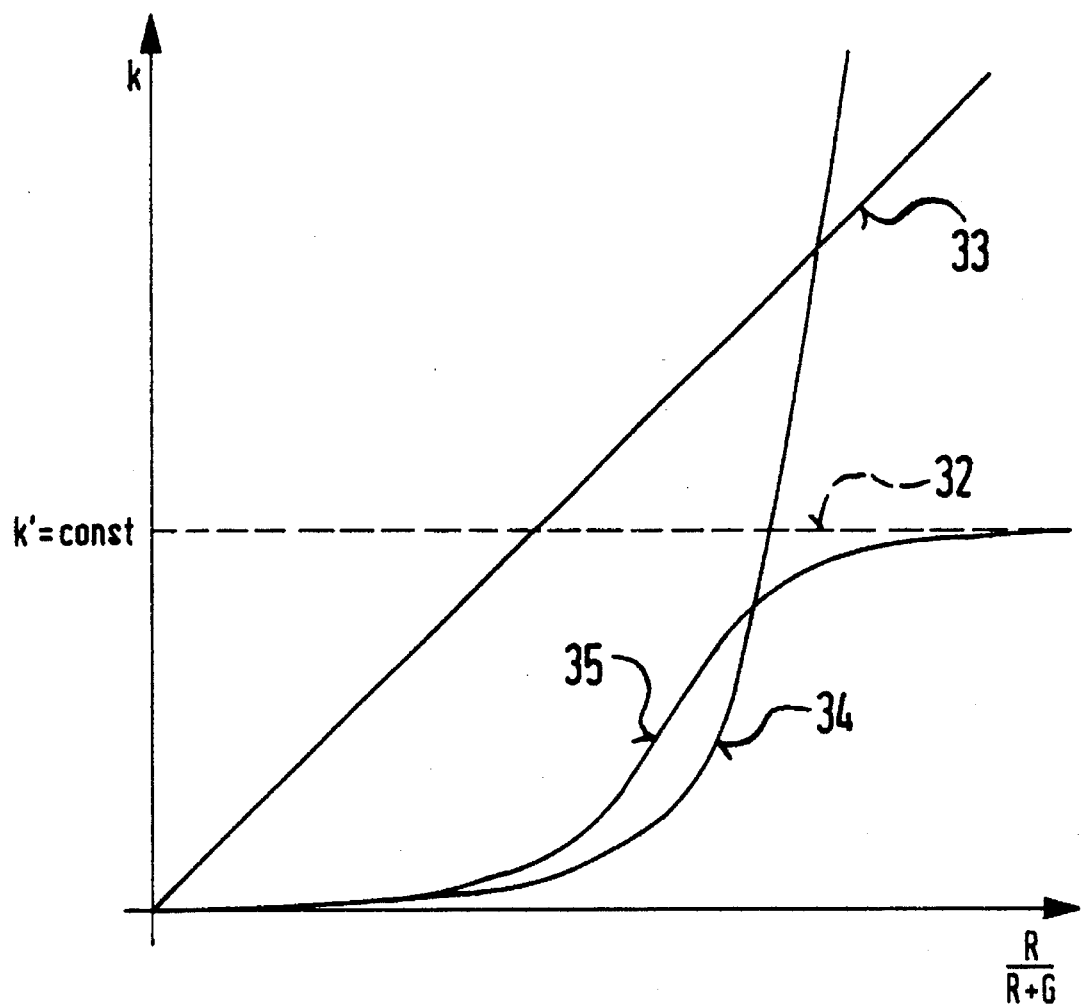
FIG. 3 is a graph showing correction value functions stored in a storage medium.

FIG. 3 shows several possible functions which can be stored in the write-read memory 22a for the correction value k in dependency upon the relationship of the red portion to the brightness portion of the color picture signal, more specifically the quotient R/(R+G).

It is expedient if each color is allocated its own correction value function, even though FIG. 3 only shows one curve for each color. The dotted straight line 32 corresponds to a static white balance correction, that is, the correction value k' is constant and is not dependent on the relationship R/(R+G). The use of such a white balance correction would have the consequence that even a picture with a small red portion would also undergo a white balance correction, and would thus exhibit a color cast outside of the operating field, or, even in the case of a long observation distance, where there was no red shift.

The straight line 33 shows a linear dynamic function as it can be used as an application-specific correction function by the correction device in accordance with the invention. Here, the correction value k increases in a linear fashion with an increasing ratio of red portion/brightness portion, or with the increasing ratio R/(R+G), of the picture. This correction value function is particularly advantageous, since in the case of a longer observation distance, the mucous membrane is not so strongly trans-illuminated, and thus the red shift is smaller than in the case of a shorter observation distance where, depending on the application, a strong red shift occurs. The white balance is thus corrected only as strongly as a shift in the red direction occurs.

In contrast with that, the functions 34 and 35 exhibit a pronounced non-linear behavior. This has the consequence that small red portions, which, for example, are not caused by a red shift, are tolerated in the picture; that is, they bring about no correction of the white balance, or only a small one. Stronger red portions, such as are brought about by a red shift that results from the mucous membrane, cause a contrastingly stronger white balance correction than in the case of linear, dynamic behavior. While the curve 34 grows continuously from a specific relationship R/(R+G), the curve 35 has an asymptotic approximation of a constant correction value; for example, in accordance with FIG. 3, of the correction value k', which corresponds to the axis-parallel straight line 32. This has the consequence that, in the case of larger red shifts, a white balance correction is carried out with an almost constant correction value k'.

However, it should be expressly mentioned that FIG. 3 only represents examples of the functions of the correction value k. Which correction value function is ultimately stored or selected depends upon the nature of the hollow organ being examined, and on the selection subsequently carried out at the control unit 21, or more specifically its keys 21a, . . . 21n by the examining person. Thus, it is entirely possible for other dynamic curves of the correction value k to be stored in the write-read memory 22a as well.

The microprocessor 22e thus generates the correction value k for the color signals RW, GW and BW in dependency upon the measured quotient R/(R+G) and on the correction value function selected from the write-read memory (FIG. 3), while the microprocessor 22e generates the respective correction values on the basis of the look-up tables corresponding to the correction value functions stored in the write-read memory. This is significantly faster than a calculation.

For the detection of the quotient R/(R+G), the video signals R and G are present at the input of the integration and retention members 22h, 22i, and are integrated over one field period; that is over 20 ms. With the negative flank of the vertical synchronization pulse $V_{sync}$, the voltage integrated over a field period is stored at the output of the integration and retention members 22h, 22i. These voltages then correspond to the intensity of the red portion and green portion of the color picture. The positive flank of the vertical synchronization pulse $V_{sync}$ reduces the integrator of the integration and retention members 22h, 22i and triggers an interruption at the microprocessor 22e. The microprocessor 22e switches a multiplexer 22g at the output of the integration and retention member 22i. As a result, the voltage of the red channel is present at the input of an analog-digital converter 22f and is digitized there. This digitized value is temporarily stored in the microprocessor 22e. With the aid of the newly detected red portion and with the aid of the green portion which is one field period older, an approximate value of the brightness signal is calculated in accordance with the sum R+G. Thereafter the quotient of the new red portion is calculated in accordance with R/(R+G).

According to this embodiment, on the basis of the quotient R/(R+G) calculated in this way, the microprocessor 22e reads the white balance corrections selected at the control unit 21 from the look-up table in the write-read memory 22a. Alternatively, the microprocessor 22e can calculate, by means of arithmetic operations, the correction values k that correspond to the quotient R/(R+G) for each color. However, this requires a longer computation time than the time needed for reading from the look-up table.

With the next vertical synchronization pulse $V_{sync}$, the described read, integration and conversion process is repeated in the same way, except that now only the green channel G is read in. To do this, the multiplexer 22g is switched over to the integration and retention member 22h. With the aid of the new green portion and with the aid of the red portion which is now one field period older, an approximation value is again calculated for the brightness portion; that is the sum R+G. Subsequent to the calculation of the quotient R/(R+G) and making use of the selected white balance correction function, the correction values k are again determined for each color once, or are read from the correction value function look-up tables stored in the write-read memory. It is thus sufficient to measure the intensity of a color component R or G and to read it into the microprocessor once per field period, since within a field period of 20 ms, the color integrated over a field period only changes by fractions.

It would also be conceivable to measure the R portion and the G portion after each frame period; that is, to read the R channel and the G channel into the microprocessor 22e and to calculate the correction value k again from that. The load on the microprocessor 22e would thereby be reduced, since it would have to carry out only half as many operations per unit of time. However, this would have the consequence that the correction voltage generators 22b, 22c, 22d are reset into a 25 Hz rhythm, and would no longer be in a 50 Hz rhythm. In extreme cases, this can lead to a flicker effect, since 25 Hz pictures lie close to the threshold of perception of the human eye.

Preferably, therefore, the red components and the green components are detected, and the digital value corresponding to their intensity is read into the microprocessor 22e, displaced from each other by one field period.

The correction voltage generators 22b, 22c and 22d represent digital-analog converters or digital potentiometers. They receive from the microprocessor 22e the digital correction values k that correspond to the individual color components and convert them into the correction voltages $U_{RW}$, $U_{GW}$, $U_{BW}$ which are directed to the control inputs of the VCAs 18a, 18b and 18c.

In addition to the selection of the correction value functions by pressing the keys 21a, . . . 21n of the control unit 21, the examining person who is handling the endoscope can also manually change the application-specific correction voltages to values that do not correspond to the values in the write-read memory 22a. By pressing one of the keys 21a, . . . 21n, this manual change can also be canceled again, so that the correction values k corresponding to the preset functions are again generated at the output of the microprocessor 22e.

Figure 4:
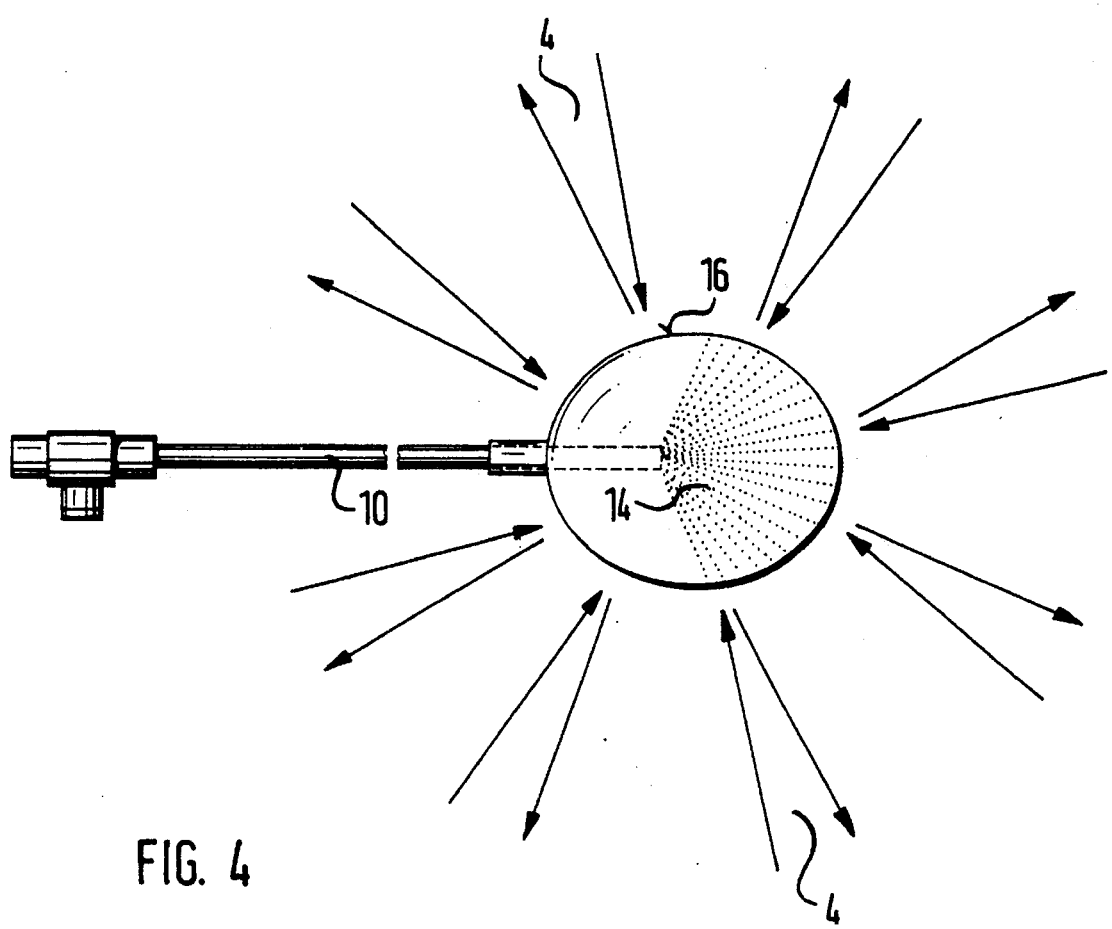
FIG. 4 is a simplified diagram of an accessory device for the automatic white balance.

Shown in FIG. 4 is an auxiliary device for the white balance carried out with the white balance device 17 shown in FIG. 1. With the auxiliary device, a white balance known as EWC (Endo White Control) is performed. In addition, the spectral differences of the components being used in the endoscopic system, such as light guides, light source and endoscope, are compensated for. The endoscope 10 is inserted through an opening into a balloon-shaped balance accessory 16 with a white coating on the inside. In this way, it is ensured that ambient light 4 that disturbs the balance cannot mix with the illumination light and lead to a false result. With the balance aid 16 and the white balance device 17 as it is known from EP-0530738A, the difference in the components being used in an endoscopic system can now be compensated for. As a result, a white field of observation located in front of the endoscope is also shown in white on the monitor.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for correcting the white balance of a video color picture signal, comprising the steps of:

a) detecting the color quality of a video color picture signal, including at least a red component (R) and a brightness portion,:

b) determining correction values (k) for correcting the color picture signal present after a white balance, for each individual color component (R, G, B) of the picture signal in dependency upon pre-set operating conditions, and c) correcting the color picture signal corresponding to the white balance using the correction values (k) determined in step (b), in dependency upon a relationship of the red component (R) detected in step (a) to the brightness portion of the detected color quality of the color picture signal.

2. The method in accordance with claim 1, further comprising a preliminary storage step wherein several sets of correction values (k) corresponding to the pre-set operating conditions are stored, and said sets are read from a storage medium in step (b).

3. The method in accordance with claim 1, wherein step (a) further includes an integration step (d) for integrating at least a portion of the color components (R, G, B) over one field period of received color picture signal.

4. The method in accordance with claim 3, wherein the integration step (d) integrates only red and green color components (R, G), and the correction step (c) corrects the color picture signal present following the white balance in dependency upon the relationship $$R/(R+G),$$

wherein R is the red component and G is the green component.

5. The method in accordance with claim 1, wherein the correction values (k) determined in step (b) are dependent upon the relationship of the red component (R) to the brightness portion of the color picture signal in a linear fashion.

6. The method in accordance with claim 1, wherein the correction values (k) determined in step (b) are dependent upon the relationship of the red component (R) to the brightness portion of the color picture signal in a non-linear fashion.

7. The method in accordance with claim 2, wherein the sets of correction values (k) stored in the storage step or several stored correction value functions are read out in dependency upon the relationship R/(R+G), wherein R is the red component and G is the green component.

8. The method in accordance with claim 2, further comprising a selection step (e) for selecting, in an application-specific manner a set desired for said application from among a number of stored sets of correction values (k), or a desired correction value function from among a number of stored functions, such that an application-specific correction is carried out in correction step (c).

9. The method for correcting the white balance of video color picture signal in accordance with claim 1, wherein the signal is used in a video endoscope or an endoscope camera.

10. An apparatus for correcting the white balance of a video color picture signal, comprising a detection device (22) for the detecting the color quality of a received color picture signal including at least a red component (R) and a brightness portion, means (22e) for the determining correction values (k) for correcting the white balance for each individual color component (R, G, B) in dependency upon preset operating conditions, and correction members (18a, 18b, 18c, 22a–22e) for the correcting the color components of the color picture signal corresponding to the white balance using the determined correction values (k) in dependency upon a relationship of the red component to the brightness portion corresponding to the color quality detected by the detection device (22).

11. The apparatus in accordance with claim 10, wherein the detection device (22) comprises members (22h, 22i) for measuring intensity of red component (R) and green component (G) of the color picture signal.

12. The apparatus in accordance with claim 11, wherein the members comprises integration and retention members (22h, 22i) for integrating and retaining the measured intensity of both the red component (R) and the green component (G) over one field period of the received color picture signal.

13. The apparatus in accordance with claim 12, further comprising an arithmetic unit (22e) for calculating a brightness signal (R+G) from the red component R and the green component (G) that were integrated and retained over one field period by the integration and retention members for calculating a quotient R/(R+G) from an instantaneously measured intensity of the red component (R) and the calculated brightness signal (R+G), and for determining the correction value.

14. The apparatus in accordance with claim 13, wherein the arithmetic unit (22e) comprises a microprocessor.

15. The apparatus in accordance with claim 14, wherein the microprocessor (22e) includes a write-read memory (22a) as storage means.

16. The apparatus in accordance with claim 15, wherein the write-read memory (22a) stores several pre-set sets of correction values (k), which are dependent upon the quotient R/(R+G) and upon the pre-set operating conditions, in the form of look-up tables, and wherein the microprocessor reads, from the look-up table corresponding to current operating conditions, an appropriate correction value (k) based on the quotient R/(R+G) calculated from the instantaneously measured intensity of red component (R) and the brightness signal (R+G).

17. The apparatus in accordance with claim 14, further comprising a control unit (21, 21a, . . . 21n) functionally connected with input of the microprocessor (22e) for selection of one of a number of sets of correction values (k) stored in the write-read memory or one of a number of correction value functions dependent upon quotients of the instantaneous red component (R) and the calculated brightness signal (R+G).

18. An apparatus in accordance with claim 14, wherein the microprocessor (22e) is connected on an output side to correction voltage generators (22b, 22c, 22d), one of which is allocated to each of the color components and receives from the microprocessor (22e) a respective selected correction value (k) for a particular color component in order to generate therefrom a DC correction voltage ($U_{RW}$, $U_{GW}$, $U_{BW}$).

19. An apparatus in accordance with claim 18, wherein each correction voltage generator (22b, 22c, 22d) includes a digital-analog converter for generating an analog DC correction voltage.

20. An apparatus in accordance with claim 19, wherein an analog output of each digital analog converter which generates at respective correction voltage ($U_{RW}$, $U_{GW}$, $U_{BW}$) is connected with an input of a voltage-controlled amplifier (18a, 18b, 18c), a different input of each voltage-controlled amplifier (18a, 18b, 18c) being connected with an output of a white balance device (17), which is in turn functionally coupled with the control unit (21, 21a, . . . 21n) for the carrying-out of an automatic white balance, and wherein outputs of three voltage-controlled amplifiers (18a, 18b, 18c) are respectively led to inputs of a matrix circuit (19) for the generating component signals (Y, U, V).

* * * * *